(12) United States Patent
Kankan et al.

(10) Patent No.: US 7,666,896 B2
(45) Date of Patent: Feb. 23, 2010

(54) PROCESS FOR THE PREPARATION OF PERINDOPRIL

(75) Inventors: Rajendra Narayanrao Kankan, Maharashtra (IN); Dharmaraj Ramachandra Rao, Maharashtra (IN)

(73) Assignee: Cipla Limited, Mumbai (IN)

( * ) Notice: Subject to any disclaimer, the term of this patent is extended or adjusted under 35 U.S.C. 154(b) by 167 days.

(21) Appl. No.: 10/599,918

(22) PCT Filed: Apr. 7, 2005

(86) PCT No.: PCT/GB2005/001355

§ 371 (c)(1),
(2), (4) Date: Apr. 9, 2007

(87) PCT Pub. No.: WO2005/100317

PCT Pub. Date: Oct. 27, 2005

(65) Prior Publication Data

US 2007/0185335 A1    Aug. 9, 2007

(30) Foreign Application Priority Data

Apr. 13, 2004  (GB) ................. 0408258.2

(51) Int. Cl.
*A61K 31/404* (2006.01)
*C07D 209/04* (2006.01)

(52) U.S. Cl. ..................... 514/412; 548/452

(58) Field of Classification Search ............ 548/452
See application file for complete search history.

(56) References Cited

U.S. PATENT DOCUMENTS

| | | |
|---|---|---|
| 4,508,729 A | 4/1985 | Vincent et al. |
| 4,914,214 A | 4/1990 | Vincent et al. |
| 4,933,361 A | 6/1990 | Urbach et al. |
| 6,818,788 B2 | 11/2004 | Souvie |
| 6,835,843 B2 | 12/2004 | Langlois et al. |
| 7,060,842 B2 | 6/2006 | Mezei et al. |
| 2007/0093663 A1 | 4/2007 | Dubuffet et al. |

FOREIGN PATENT DOCUMENTS

| | | |
|---|---|---|
| EP | 0308341 A1 | 3/1989 |
| EP | 1256590 A1 | 11/2002 |
| EP | 1420029 A2 | 5/2004 |
| WO | 0156353 A2 | 8/2001 |
| WO | 0158868 A1 | 8/2001 |
| WO | 2004046172 A1 | 6/2004 |
| WO | 2004099138 A2 | 11/2004 |

OTHER PUBLICATIONS

Pascard, Claudine, et al., "Configuration and Preferential Solid-State Conformations of Perindoprilat (S-9780). Comparison with the Crystal Structures of Other ACE Inhibitors and Conclusions Related to Structure-Activity Relationships," vol. 34, No. 2 (1991), Journal of Medicinal Chemistry, American Chemical Society, pp. 663-669.

Vincent, M., et al., "Stereoselective Synthesis of a New Perhydroindole Derivative of Chiral Iminodiacid, A Potent Inhibitor of Angiotensin Converting Enzyme," vol. 23, No. 16, Tetrahedron Letters (1982), Pergamon Press Ltd., Great Britain, pp. 1677-1680.

Foreign communication from a related counterpart application—International Search Report, PCT/GB2005/001355, Sep. 8, 2005, 7 pgs.

Foreign communication from a related counterpart application—International Preliminary Report on Patentability, PCT/GB2005/001355, Oct. 19, 2006, 10 pgs.

*Primary Examiner*—Kamal A Saeed
*Assistant Examiner*—Kristin Bianchi
(74) *Attorney, Agent, or Firm*—Conley Rose, P.C.; Rodney B. Carroll

(57) ABSTRACT

A process for preparing perindopril (III) or a pharmaceutically acceptable salt thereof, which process comprises a substituted benzyl ester of (2S,3aS,7aS)-octahydroindole-2-carboxylic acid (I) with N—[(S)-carbethoxybutyl]-(S)-alanine (II) where R represents a halo, $C_{1-4}$ alkoxy or nitro substituent.

19 Claims, No Drawings

PROCESS FOR THE PREPARATION OF PERINDOPRIL

The present invention relates to a process for preparing perindopril and pharmaceutically acceptable salts thereof.

Perindopril is the international non-proprietary name of (2S,3aS,7aS)-1-{2-[1-(ethoxycarbonyl)-(S)-butylamino]-(S)-propionyl}-octahydroindole-2-carboxylic acid. Perindopril is known to have therapeutic application as an angiotensin-converting enzyme (ACE) inhibitor. ACE is a peptidyl dipeptidase which catalyzes the conversion of angiotensin I to angiotensin II, as well as causing the degradation of bradykinin. Angiotensin II is a vasoconstrictor which also stimulates aldosterone secretion by the adrenal cortex. Inhibition of ACE has, therefore, been shown to have therapeutic utility in patients suffering from disease states such as hypertension and congestive heart failure. In addition, it has been discovered that ACE inhibitors are useful in treating cognitive disorders.

Perindopril has the following structural formula (I)

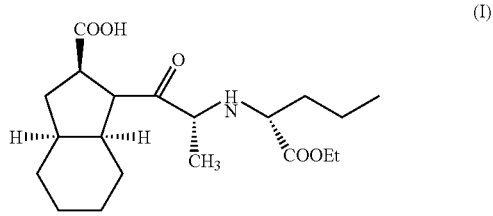

Perindopril is described in U.S. Pat. No. 4,508,729. Preparative processes described in this U.S. patent are carried out in an alcoholic medium, and in the presence of a neutral dehydrating agent and an organic or inorganic cyanoborohydride. Deprotection processes can be carried out where necessary, for example with reference to hydrolysis and/or hydrogenolysis. U.S. Pat. No. 4,508,729 also describes the hydrogenation of (2S)-2-ethoxycarbonylindoline (which is now known as S-indoline-2-carboxylic acid) as a hydrochloride to (2S)-2-ethoxycarbonylperhydroindole (now (2S,3aS,7aS)-octahydroindole-2-carboxylic acid). The reaction is done in acidic pH and the pressure required is 50 kg/cm$^2$.

U.S. Pat. No. 4,914,214 describes a process for the preparation of the benzyl ester of (2S,3aS,7aS)-octahydroindole-2-carboxylic acid. In the preparation of the benzyl ester of perhydroindole-2-carboxylic acid, an excess of p-toluene sulphonic acid is used. This excess of p-toluene sulphonic acid has been found to be detrimental to the purity of the product. U.S. Pat. No. 4,914,214 also describes a process for the preparation of perindopril and its t-butylamine salt. The process comprises condensation of the p-toluene sulphonic acid salt of the benzyl ester of (2S,3aS,7aS)-octahydroindole-2-carboxylic acid with N—[(S)-1-carbethoxybutyl]-(S)-alanine, followed by deprotection employing charcoal containing 5% palladium and water. Tertiary-butylamine is then added to yield the t-butylamine salt of perindopril. The coupling step is carried out in the presence of N,N-dicyclohexyl carbodiimide (DCC) and 1-hydroxybenzotriazole (HOBT). Due to the presence of p-toluene sulphonic acid, a 3-fold excess of triethylamine and the coupling reagents have to be used.

An improved process for the above coupling step is described in WO 01/58868 where little or no triethylamine, 1 to 1.2 moles of DCC and 0.4 to 0.6 moles of HOBT are used and the reaction is done above 20° C. It has, however, been observed that with 1.2 moles of DCC under the conditions mentioned in the patent there is some unreacted ester in the reaction.

Tetrahedron Letters Vol. 23, No. 16, pp 1677-80, 1982 describes a process for preparation of N—[(S)-1-carbethoxybutyl]-(S)-alanine by reaction of norvaline ethyl ester with pyruvic acid in ethanol under reductive amination conditions to get a 7:3 mixture of isomeric compounds that are separated by first preparing the hydrochloride in ethyl acetate to filter off the unrequired isomer. The filtrate is evaporated to dryness and the residue is purified by applying to Dowex 50 H+ resin and eluting with ammonia followed by crystallization from acetonitrile.

There is now provided by the present invention, however, an improved process for the preparation of perindopril, or a pharmaceutically acceptable salt thereof, which process has been modified over the disclosure of the prior art processes, and now alleviates many of the above described problems associated with the prior art processes.

In one aspect, the present invention provides a process for preparing perindopril, or a pharmaceutically acceptable salt thereof, which process comprises coupling a substituted benzyl ester of (2S,3aS,7aS)-octahydroindole-2-carboxylic acid (I) with N—[(S)-carbethoxybutyl]-(S)-alanine (II):

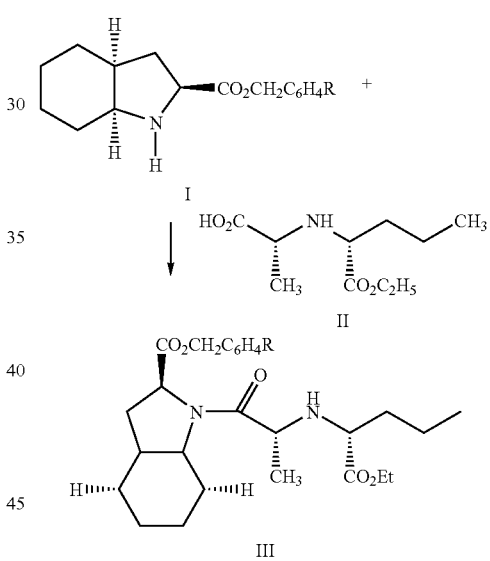

where R represents at least one ring substituent, preferably a halo, $C_{1-4}$ alkoxy or nitro substituent, to form the ester of formula III, wherein the coupling is carried out in the presence of N,N-dicyclohexyl carbodiimide (DCC) and 1-hydroxybenzotriazole (HOBT): and converting the ester of formula III to perindopril or a pharmaceutically acceptable salt thereof. This low temperature process avoids impurity formation that can be associated with prior art procedures, and also provides advantages in the choice of protecting group.

In another aspect, the invention provides a process for preparing perindopril, or a pharmaceutically acceptable salt thereof, which includes an intermediate process step wherein an aralkyl ester of (2S,3aS,7aS)-octahydroindole-2-carboxylic acid is prepared by reaction of (2S,3aS,7aS)-octahydroindole-2-carboxylic acid with an aralkyl alcohol, wherein either said (2S,3aS,7aS)-octahydroindole-2-carboxylic acid is treated with an excess of the alcohol and thionyl chloride, excess alcohol is distilled off and the residue treated with a solvent to obtain the aralkyl ester of (2S,3aS,7aS)-octahydroindole-2-carboxylic acid as a hydrochloride; or said (2S, 3aS,7aS)-octahydroindole-2-carboxylic acid is treated with an excess of the alcohol and heated with toluene using a molar quantity p-toluene sulphonic acid, to obtain the aralkyl ester of (2S,3aS,7aS)-octahydroindole-2-carboxylic acid as a base.

In another aspect, the invention provides a process for preparing perindopril, or a pharmaceutically acceptable salt thereof, which includes an intermediate process step which comprises conversion of an alkali metal salt of S-indoline-2-carboxylic acid to (2S,3aS,7aS)-octahydroindole-2-carboxylic acid by hydrogenation at a pressure of from 5 to 20 bar, and the product is crystallized from acetonitrile. This aspect provides a simplified intermediate process step for preparation of (2S,3aS,7aS)-octahydroindole-2-carboxylic acid by hydrogenation of S-indoline-2-carboxylic acid under reduced pressure conditions, when compared to the process disclosure of prior art U.S. Pat. No. 4,508,729.

In another aspect, the invention provides a process for preparing perindopril, or a pharmaceutically acceptable salt thereof, which includes an intermediate process step which comprises condensation of norvaline ethyl ester with pyruvic acid to yield N—[(S)-1-carbethoxybutyl]-(S)-alanine (II), wherein said condensation is carried out under catalytic hydrogenation and said catalyst and any inorganic salts present in the reaction medium are removed by filtration to obtain a filtrate, the filtrate is concentrated and N—[(S)-1-carbethoxybutyl]-(S)-alanine is isolated by precipitation by the addition of a solvent selected from acetone and ethyl acetate. This aspect provides a simplified work-up procedure in the intermediate process step of obtaining the amino-acid ester, namely N—[(S)-1-carbethoxybutyl]-(S)-alanine, in good yield, when compared to the above described techniques of separation, resin purification and crystallization of the prior art article in Tetrahedron letters.

In the process of the first aspect of the invention, R represents a 4-halo, 4-$C_{1-4}$alkoxy or 4-nitro substituent, and the coupling is carried out in the presence of N,N-dicyclohexyl carbodiimide (DCC) and 1-hydroxybenzotriazole (HOBT). Preferably, the coupling is carried out at a temperature of below about 20° C., and about 1.5 to 1.7 moles of DCC are employed.

Preferably R represents a 4-chloro or 4-methoxy substituent, with 4-chloro being preferred.

The above operation at a low temperature of below about 20° C. is advantageous in obviating impurity formation associated with prior art procedures and also the use of DCC in molar proportion of 1.5 to 1.7 achieves substantially complete conversion of the substituted benzyl ester of (2S,3aS,7aS)-octahydroindole-2-carboxylic acid to perindopril. Typically, the coupling is carried out at a temperature in the range of 10-15° C.

The above coupling initially results in the formation of 4-substituted benzyl perindopril, which is converted to perindopril free base by deprotection in an alcoholic solvent, such as IPA, suitably using palladium on carbon as a catalyst. The perindopril free base is then advantageously converted to a pharmaceutically acceptable salt thereof, with the formation of the erbumine salt being particularly preferred.

In the second aspect of the present invention, there is provided a process for preparing perindopril, or a pharmaceutically acceptable salt thereof, which includes an intermediate process step wherein the above substituted benzyl ester of (2S,3aS,7aS)-octahydroindole-2-carboxylic acid is prepared by reaction of (2S,3aS,7aS)-octahydroindole-2-carboxylic acid with the corresponding substituted benzyl alcohol, namely 4-halo-benzyl alcohol, 4-$C_{1-4}$-alkoxy benzyl alcohol, or 4-nitro-benzyl alcohol, as follows:

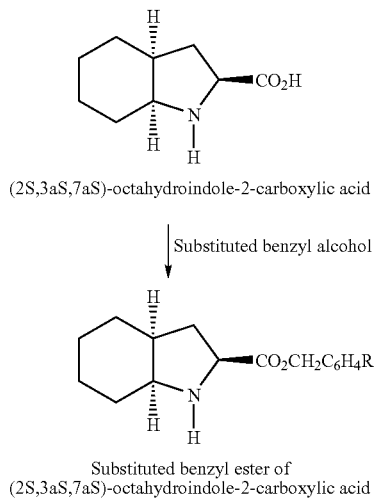

(2S,3aS,7aS)-octahydroindole-2-carboxylic acid

↓ Substituted benzyl alcohol

Substituted benzyl ester of (2S,3aS,7aS)-octahydroindole-2-carboxylic acid

The esters may be prepared by treating the acid with an excess of alcohol and thionyl chloride and distilling off the excess alcohol and treating the residue with a suitable solvent such as ethyl ether to obtain the ester as a hydrochloride; alternatively the acid and an excess of alcohol are heated with toluene using molar quantity p-toluene sulphonic acid and obtaining the ester as a base after a suitable work-up. These procedures according to the present invention alleviate the lack of purity associated with the prior art techniques.

In the third aspect of the present invention, there is provided a process for preparing perindopril, or a pharmaceutically acceptable salt thereof, which includes an intermediate process step which comprises conversion of S-indoline-2-carboxylic acid (as an alkali metal salt) to above (2S,3aS,7aS)-octahydroindole-2-carboxylic acid. The hydrogenation is carried out at medium pressure, with a preferred operating pressure being in the range of about 5 to 20 bar, more preferably in the range of about 10 to 15 bar and even more preferably at about. 12 bar. Preferably, the hydrogenation is carried out under alkaline conditions.

Suitably S-indoline-2-carboxylic acid is employed in the hydrogenation reaction in the form of an alkali metal salt, typically the sodium salt further to the inclusion of the S-indoline-2-carboxylic free acid and a base such as sodium hydroxide in the reaction medium.

Preferably the hydrogenation is carried out in a polar solvent selected from $C_{1-4}$ alcohols and water, or mixtures thereof. Most preferably the hydrogenation solvent is water.

A preferred catalyst is 5% rhodium on alumina, although other supports can be used with similar results. Advantageously, however, the use of rhodium on alumina allows repeated recycling of the catalyst with substantially no loss in activity.

In a further aspect of the present invention, there is provided a process for preparing perindopril, or a pharmaceutically acceptable salt thereof, which includes an intermediate process step which comprises condensation of norvaline ethyl ester with pyruvic acid to yield the above referred to N—[(S)-1-carbethoxybutyl]-(S)-alanine.

The condensation is carried out under catalytic hydrogenation and the catalyst and any inorganic salts present in the reaction medium are removed by filtration to obtain a filtrate, the filtrate is concentrated, and the N—[(S)-1-carbethoxybutyl]-(S)-alanine is isolated by precipitation by the addition of acetone or ethyl acetate.

Suitably, the norvaline ethyl ester is included in the reaction medium as the hydrochloride salt thereof, in the presence of a base, such as sodium hydroxide, so as to convert the norvaline ethyl ester hydrochloride to the free base form shown above, suitable for subsequent reaction with the pyruvic acid. The norvaline ethyl ester hydrochloride can suitably be prepared from norvaline, by techniques well known in the art.

Preferably, the catalytic hydrogenation is carried out in a hydrogenator, in the presence of palladium on carbon as the catalyst, typically 10% palladium on carbon, and suitably hydrogenation is carried out at a pressure in the range of 5 to 10 bar, preferably about 7 bar, for a period of about 8 hours.

Typically, the filtration stage of the above intermediate process step involves filtration over celite together with washing, suitably employing ethanol or other suitable washing agent. Preferably, the resulting filtrate is concentrated under vacuum, typically at about 50° C. As indicated above the precipitation solvent for N—[(S)-1-carbethoxybutyl]-(S)-alanine is selected from acetone, acetonitrile or ethyl acetate, and in a preferred embodiment acetone is employed.

The present invention thus now provides an improved overall synthesis for the preparation of perindopril, or a pharmaceutically acceptable salt thereof, which alleviates many of the problems associated with the prior art, which overall synthesis can be illustrated by the following reaction scheme:

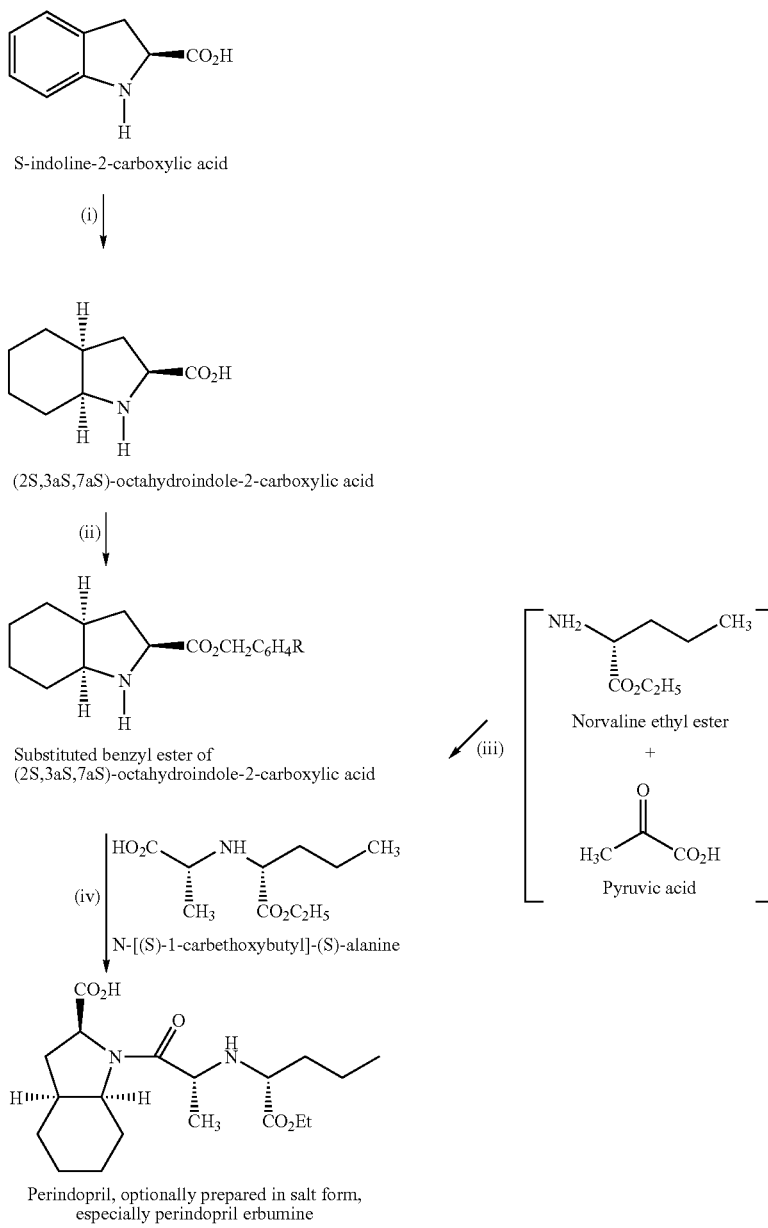

The reaction conditions in each of steps (i) to (iv) as shown in the overall scheme are as described above in relation to each of the respective intermediate steps. More particularly, for step (i), the hydrogenation is carried out at medium pressure; for step (ii), this alleviates impurity problems associated with the prior art and involves ester preparation by treating the acid with an excess of alcohol and thionyl chloride and distilling off the excess alcohol and treating the residue with a suitable solvent such as ethyl ether to obtain the ester as a hydrochloride, alternatively the acid and an excess of alcohol are heated with toluene using molar quantity p-toluene sulphonic acid and obtaining the ester as a base after a suitable work-up; for step (iii), the catalyst and any inorganic salts present in the reaction medium are removed by filtration to obtain a filtrate, the filtrate is concentrated and N—[(S)-1-carbethoxybutyl]-(S)-alanine is isolated by precipitation by the addition of acetone or ethyl acetate; and for step (iv), the coupling is carried out in the presence of N,N-dicyclohexyl carbodiimide (DCC) and 1-hydroxybenzotriazole (HOBT), and the coupling is preferably carried out at a temperature of below about 20° C., and preferably about 1.5 to 1.7 moles of DCC are employed.

Perindopril as provided by a process according to the present invention has therapeutic utility as an ACE inhibitor.

In addition, the present invention further provides a method of inhibiting ACE in a patient in need thereof comprising administering to said patient an effective ACE inhibitory amount of perindopril (preferably perindopril erbumine) as provided according to the present invention.

The present invention also provides use of perindopril as provided according to the present invention (preferably perindopril erbumine) in the manufacture of a medicament for inhibiting ACE.

A patient can be in need of treatment to inhibit ACE, for example when the patient is suffering from hypertension, chronic congestive heart failure, or the like. Inhibition of ACE reduces levels of angiotensin II and thus inhibits the vasopressor, hypertensive and hyperaldosteronemic effects caused thereby. Inhibition of ACE would also potentiate endogenous levels of bradykinin. An effective ACE inhibitory amount of perindopril as provided according to the present invention is that amount which is effective in inhibiting ACE in a patient in need thereof which results, for example, in a hypotensive effect.

In effecting treatment of a patient, perindopril as provided according to the present invention can be administered in any form or mode which makes the compound bioavailable in effective amounts, including oral and parenteral routes. For example, perindopril as provided according to the present invention can be administered orally, subcutaneously, intramuscularly, intravenously, transdermally, intranasally, rectally, and the like. Oral administration is generally preferred. One skilled in the art of preparing formulations can readily select the proper form and mode of administration depending upon the disease state to be treated and the stage of the disease.

Perindopril as provided according to the present invention can be administered in the form of pharmaceutical compositions or medicaments which are prepared by combining the perindopril according to the present invention with pharmaceutically acceptable carriers, diluents or excipients therefor, the proportion and nature of which are determined by the chosen route of administration, and standard pharmaceutical practice.

In another embodiment, the present invention provides pharmaceutical compositions comprising an effective ACE inhibitory amount of perindopril as provided according to the present invention (preferably perindopril erbumine), together with one or more pharmaceutically acceptable carriers, diluents or excipients therefor.

By "pharmaceutically acceptable" it is meant that the carrier, diluent or excipient must be compatible with perindopril as provided according to the present invention, and not be deleterious to a recipient thereof.

The pharmaceutical compositions or medicaments are prepared in a manner well known in the pharmaceutical art. The carrier, diluent or excipient may be a solid, semi-solid, or liquid material, which can serve as a vehicle or medium for the active ingredient. Suitable carriers, diluents or excipients are well known in the art. Pharmaceutical compositions according to the present invention may be adapted for oral or parenteral use and may be administered to the patient in the form of tablets, capsules, suppositories, solutions, suspensions or the like.

The pharmaceutical compositions may be administered orally, for example, with an inert diluent or with an edible carrier. They may be enclosed in gelatin capsules or compressed into tablets. For the purpose of oral therapeutic administration, perindopril as provided by the present invention may be incorporated with excipients and used in the form of tablets, capsules, elixirs, suspensions, syrups and the like.

The tablets, pills, capsules, and the like may also contain one or more of the following adjuvants: binders, such as microcrystalline cellulose, gum tragacanth or gelatin; excipients, such as starch or lactose; disintegrating agents such as alginic acid, corn starch and the like; lubricants, such as magnesium stearate; glidants, such as colloidal silicon dioxide; and sweetening agents, such as sucrose or saccharin. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives. Materials used in preparing these various compositions should be pharmaceutically pure and non-toxic in the amounts used.

For the purpose of parenteral administration perindopril as provided according to the present invention may be incorporated into a solution or suspension. The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; and buffers such as acetates, citrates or phosphates. The parenteral preparation can be enclosed in ampoules, disposable syringes or multiple dose vials made of glass or plastic.

The present invention will now be further illustrated by the following Examples, which do not limit the scope of the invention in any way.

EXAMPLE 1

Preparation of
N—[(S)-1-carbethoxybutyl]-(S)-alanine

L-Norvaline ethyl ester hydrochloride (50 gm) was dissolved in ethanol (600 ml). Sodium hydroxide (15.4 gm) dissolved in ethanol (500 ml) was added to the above at 10° C.

and stirred for 30 minutes. Pyruvic acid (34.5 gm) solution in ethanol (200 ml) was then added to above reaction mass at 10° C. and stirred for 30 minutes. The reaction mass was then transferred to a hydrogenator along with 10% palladium on carbon (5 gm) and hydrogenated at 7 bar for 8 hours. The contents were filtered over celite and washed with ethanol (200 ml). The filtrate was concentrated completely under vacuum at about 50° C. Acetone (800 ml) was added to the residue and the contents refluxed for 1 hour and then cooled to room temperature and filtered to obtain the product (30 gm) as white crystals.

EXAMPLE 2

Preparation of 2S,3aS,7aS-Octahydroindole-2-Carboxylic Acid

S-Indoline-2-carboxylic acid (50 gm) (0.31 mole), sodium hydroxide (12.27 gm) (0.31 mole), 5% rhodium on alumina (7.5 gm), were mixed with water (1 lit) in an autoclave and hydrogenated at a pressure of 12 bar at 50° C. The catalyst was filtered off and the bed washed with water (200 ml). The reaction mass was cooled to 15-20° C. and acidified to pH 3.0 to 3.2 using conc. HCl and washed with (4×250 ml) ethyl acetate. The pH of the aqueous phase was adjusted to 6.5 with 10% sodium hydroxide solution. Water was then removed by distillation under vacuum and the traces were further removed by addition of toluene and continuing the distillation. The product was isolated by addition of acetonitrile (500 ml) and filtration. The crude product was recrystallized from methanol to give the title compound (40 gm).

EXAMPLE 3

Preparation of 2S,3aS,7aS-Octahdroindole-2-carboxylic acid-4-chlorophenylmethyl ester 2S,3aS,7aS-Octahydroindole-2-carboxylic acid (50 gm) (0.3 mole), 4-chlorobenzyl alcohol (46.37 gm) (0.33 mol), p-toluene sulfonic acid (67.52 gm) (0.35 mol), and toluene (400 ml) were heated to reflux temperature and water removed azeotropically. The contents were cooled and water (100 ml) was added and stirred for 15 minutes. The lower aqueous layer was discarded and the toluene was distilled under vacuum at 60° C. to get an oil. Diisopropyl ether (200 ml) was added to the residue and stirred at room temp.

The solids were filtered and the wet cake was added to dichloromethane (500 ml) and aqueous ammonia (60 ml) was added dropwise under stirring. The aqueous phase was separated and the organic phase washed with water till the washings were neutral. Dichloromethane was concentrated at 50° C. under vacuum to get oil (37.2 gm) which solidifies on standing.

EXAMPLE 4

Preparation of Perindopril Erbumine

The oil obtained from Example 3 (24 gm) was dissolved in dichloromethane (230 ml) and cooled below 10° C. 1-hydroxybenzotriazole (6 gm) and N—[(S)-1-carbethoxybutyl]-(S)-alanine (21.26 gm) were added to the reaction mass. The solution of DCC (25 gm) in MDC (100 ml) was added drop wise to the reaction mass below 15° C. in about 60 min. The reaction mass was stirred for 4 hrs at 10-15° C. and was filtered through celite. The filtrate was then washed with saturated solution of sodium bicarbonate followed by water. Dichloromethane was concentrated at 50° C. under vacuum to get oil which was dissolved in diisopropyl ether and chilled to 10° C., stirred for 30 min and filtered through celite. The filtrate was then concentrated to get a yellowish oil (43 gm).

The oil was dissolved in isopropyl alcohol (430 ml). Tertbutyl amine (20.5 gm) was added and hydrogenated at 40 psi for 3 hrs using 10% Pd/C (50% wet, 7 gm). After completion of reaction catalyst was filtered through celite and the filtrate was vacuum distilled below 40° C. Traces of isopropyl alcohol were removed by co-distilling with acetone (400 ml) under vacuum. Acetone (100 ml) was added, warmed up to 45-50° C., and stirred for 30 min. It was then cooled to 10-15° C., filtered and washed with acetone. After drying at 40° C., perindopril erbumine (20.5 gm) was obtained as white crystalline solid.

The invention claimed is:

1. A process for preparing perindopril, or a pharmaceutically acceptable salt thereof, which process comprises:
   (i) condensation of norvaline ethyl ester with pyruvic acid to yield N—[(S)-1-carbethoxybutyl]-(S)-alanine (II), wherein said condensation is carried out under catalytic hydrogenation at a pressure ranging from 5 to 10 bars and said catalyst and any inorganic salts present in the reaction medium are removed by filtration to obtain a filtrate, the filtrate is concentrated and N—[(S)-1-carbethoxybutyl]-(S)-alanine is isolated by precipitation by the addition of a solvent selected from acetone and ethyl acetate;

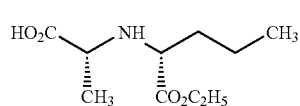

(ii) conversion of an alkali metal salt of S-indoline-2-carboxylic acid to (2S,3aS,7aS)-octahydroindole-2-carboxylic acid by hydrogenation using 5% rhodium on alumina at a pressure of from 5 to 20 bar;
   (iii) preparing a substituted benzyl ester of the (2S,3aS,7aS)-octahydroindole-2-carboxylic acid (I), by reaction of (2S,3aS,7aS)-octahydroindole-2-carboxylic acid with the corresponding substituted benzyl alcohol of formula HOCH$_2$C$_6$H$_4$R, wherein either said (2S,3aS,7aS)-octahydroindole-2-carboxylic acid is treated with an excess of the alcohol and thionyl chloride, excess alcohol is distilled off and the residue treated with a solvent to obtain the substituted benzyl ester of (2S,3aS,7aS)-octahydroindole-2-carboxylic acid as a hydrochloride; or said (2S,3aS,7aS)-octahydroindole-2-carboxylic acid is treated with an excess of the alcohol and heated with toluene using a molar quantity of p-toluene sulphonic acid, to obtain the substituted benzyl ester of (2S,3aS,7aS)-octahydroindole-2-carboxylic acid as a salt, and converting the salt to the base, preferably by treatment with ammonia; and

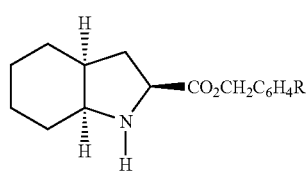

(iv) coupling the substituted benzyl ester of (2S,3aS,7aS)-octahydroindole-2-carboxylic acid (I) from step (iii) with the N—[(S)-carbethoxybutyl]-(S)-alanine (II) from step (i)

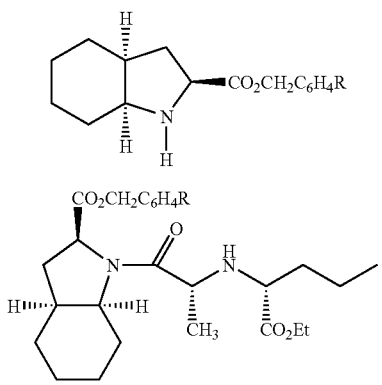

to form the ester of formula III,

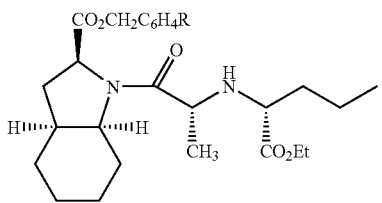

wherein the coupling is carried out in the presence of N,N-dicyclohexyl carbodiimide (DCC) and 1-hydroxybenzotriazole (HOBT); and converting the ester of formula III to perindopril or a pharmaceutically acceptable salt thereof.

2. The process according to claim 1, wherein R represents a 4-substituent.

3. The process according to claim 1, wherein the coupling in step (iv) is carried out at a temperature below 20° C.

4. The process according to claim 1, wherein from 1.5 to 1.7 mole DCC are employed per mole of the ester of formula I.

5. The process according to claim 1, which includes deprotection of the compound of formula III by hydrogenolysis in the presence of a noble metal catalyst.

6. The process according to claim 5, wherein the catalyst is palladium on carbon.

7. The process according to claim 1, wherein the perindopril is converted to a pharmaceutically acceptable salt.

8. The process according to claim 7, wherein the perindopril is converted to the tert butyl amine salt.

9. The process according to claim 1, wherein the hydrogenation in step (ii) is carried out at a pressure of 10 to 15 bar.

10. The process according to claim 1, wherein said hydrogenation in step (ii) is effected in the presence of alkali and the octahydroindole-2-carboxylic acid salt so formed is treated with mineral acid to release the free acid.

11. The process according to claim 1, wherein the alkali metal salt of said S-indoline-2-carboxylic acid is the sodium salt.

12. The process according to claim 1, wherein the hydrogenation in step (ii) is carried out in a polar solvent selected from $C_{1-4}$ alcohols and water, or mixtures thereof.

13. The process according to claim 1, wherein the product of step (ii) is crystallized from acetonitrile.

14. The process according to claim 1, wherein the condensation in step (i) is effected in ethanol.

15. The process according to claim 1, wherein said norvaline ethyl ester is included in the reaction medium as the hydrochloride salt thereof, in the presence of a base.

16. The process according to claim 1, wherein said catalytic hydrogenation is carried out in a hydrogenator, in the presence of palladium on carbon as the catalyst.

17. The process according to claim 16, wherein said catalyst is 10% palladium on carbon.

18. The process according to claim 1, wherein the precipitation solvent for N—[(S)-1-carbethoxybutyl]-(S)-alanine in step (i) is acetone.

19. The process according to claim 1, which further comprises converting perindopril free base to perindopril erbumine.

* * * * *

UNITED STATES PATENT AND TRADEMARK OFFICE
CERTIFICATE OF CORRECTION

PATENT NO. : 7,666,896 B2
APPLICATION NO. : 10/599918
DATED : February 23, 2010
INVENTOR(S) : Rajendra Narayanrao Kankan et al.

It is certified that error appears in the above-identified patent and that said Letters Patent is hereby corrected as shown below:

In Column 11, Lines 5 - 22, delete Formula I and III.

Signed and Sealed this

First Day of June, 2010

David J. Kappos
*Director of the United States Patent and Trademark Office*